United States Patent [19]

Hiji

[11] Patent Number: 5,116,820
[45] Date of Patent: May 26, 1992

[54] INTESTINAL ABSORPTION INHIBITING AGENT

[76] Inventor: Yasutake Hiji, c/o Tottori University School of Medicine, 86, Nishi-machi, Yonago-shi, Tottori-ken, Japan

[21] Appl. No.: 563,734

[22] Filed: Aug. 6, 1990

Related U.S. Application Data

[63] Continuation of Ser. No. 418,715, Oct. 3, 1989, abandoned, which is a continuation of Ser. No. 34,957, Apr. 6, 1987, abandoned.

[30] Foreign Application Priority Data

Apr. 4, 1986 [JP] Japan .................................. 61-77725

[51] Int. Cl.⁵ .................. A61K 31/70; A61K 31/715; A21D 10/00
[52] U.S. Cl. ........................................ 514/25; 514/54; 426/549
[58] Field of Search ....................... 514/23, 53, 54, 25; 536/1.1; 426/549

[56] References Cited

U.S. PATENT DOCUMENTS

| | | | |
|---|---|---|---|
| 3,875,308 | 4/1975 | Kato et al. | 426/804 |
| 3,931,146 | 1/1976 | Kato et al. | 536/1.1 |
| 4,018,233 | 4/1977 | Miyake | 536/1.1 |
| 4,370,472 | 1/1983 | Igarashi et al. | 536/1.1 |
| 4,629,725 | 12/1986 | Hiji | 514/60 |
| 4,761,286 | 8/1988 | Hiji | 424/195.1 |

FOREIGN PATENT DOCUMENTS 59-74976  4/1984  Japan .
1346756  2/1974  United Kingdom .

OTHER PUBLICATIONS

Yoshioka, Chem. Abst. 105: 35436k 1986.
Shipman and Fan, 1978, Process Biochemistry 13(3) 19–21.
Hannyan, 1984, Food Engineering 56 (3) 98–99.
Anon, 1984, Food Engineering 56(11) 88.
Chem. Abs. 95: 1482812, 1981.
Chem. Abs. 77: 101973g, 1972.
Chem. Abs. 79: 124843c, 1978.
Steinmetz Codet Ueg established 1951.

*Primary Examiner*—John W. Rollins
*Attorney, Agent, or Firm*—Armstrong & Kubovcik

[57] ABSTRACT

Intestinal absorption inhibiting agent for inhibiting glucose absorption through intestinal tracts of humans and like, the agent containing gymnemic acid and pullulan which work synergistically with each other against glucose absorption.

3 Claims, 2 Drawing Sheets

INTESTINAL ABSORPTION INHIBITING AGENT

This application is a continuation of application Ser. No. 418,715, filed Oct. 3, 1989, now abandoned, which is a continuation of application Ser. No. 034,957, filed Apr. 6, 1987, now abandoned.

BACKGROUND OF THE INVENTION

The present invention relates to low-calorie foods and beverages, and more particularly, to intestinal absorption inhibiting agents to be used in low-calorie foods and beverages.

As life becomes luxurious, people tend to ingest more foods and beverages than they need, resulting in a notable increase in obesity. At the present time, where the preference for sweet foods is strong, the amount of intake of carbohydrates is more significant for preventing obesity than that of lipids, and therefore, it is necessary not to ingest excessive sugar, starch and the like.

However, restricting the intake of sweet foods and processed starch foods results in frustration and stress build up.

Taking account of the fact that all carbohydrates are decomposed to glucose and then absorbed through the intestinal tract, if it could be arranged to inhibit absorption of glucose through the intestinal tract, this will result in control of the amount of intake of carbohydrates and enable obesity to be prevented while avoiding frustration.

Research has been undertaken from the above viewpoint and it has been heretofore considered that a certain kind of polysaccharide (as exemplified by dextran) has the effect of controlling the increase in blood glucose level which arises after sugar (sucrose) intake and that a low-calorie food or beverage effective for preventing obesity may be obtained by adding such a polysaccharide to sugar (sucrose) and the like.

However, it has been found that such a polysaccharide does not inhibit absorption of sugar through the intestinal tract and even if this polysaccharide is present, glucose is normally absorbed from the intestinal tract. Thus, it has been found that ingestion of that kind of polysaccharide contributes nothing to reduction of the calorie intake of sugar.

The Food Indication Permission Standard established by the Ministry of Public Welfare of Japan defines "a low-calorie food" as —a food of which calorie intake is less than 50% of that of an ordinary food of the same kind—. Even if the increase in blood glucose level is reduced by 50% from a normal level with use of the polysaccharide, this does not directly lead to reduction of the calorie intake by one half. The reason is that if a hormone (for example, insulin) is secreted in a large amount, the blood glucose level is seemingly reduced.

Accordingly, even if only reduction of the blood glucose level is taken into consideration, a low-calorie food or beverage effective for preventing obesity cannot be provided.

SUMMARY OF THE INVENTION

In view of the above-mentioned circumstances, the present invention aims at providing foods and beverages having low-calorie values effective by inhibiting glucose absorption through intestines.

The invention is characterized in that gymnemic acid (also called "GA") and pullulan are added to low-calorie foods and beverages as agents to inhibit intestinal absorption of glucose in humans or other animals.

Gymnemic acid is present as a primary constituent in the plant Gymnema sylvestre (hereinafter referred to as "GS") and is a saponin derived from a combination of aglycon of triterpene strain with one glucuronic acid. GS is a plant which belongs to the family of asclepiadaceae which grows naturally in the tropics and in subtropical zones ranging from India to China. Gymnemic acid is extracted from the leaves of GS and is available at relatively high cost.

Pullulan is a naturally occurring polysaccharide which was first manufactured in 1978 on a commercial basis by cultivating Aureobasidium pullulans in a stirred culture medium under aerobic conditions. Pullulan is available at low cost and has already been used in food processing and, by virtue of its indigestibility by the endogenic digestive enzymes, it has also been used in low-calorie diets.

Pullulan is a polymer containing a α-1,6-bonded portion that contributes to suppressing intestinal absorption of glucose. However, since the α-1,6-bonded portion of the pullulan constitutes only 30% of the compound, the remaining portion being α-1,4-bonded, pullulan does not have so strong an intestinal absorption inhibitory effect. However, pullulan shows no toxicity in acute, semi-acute, and chronic toxicity tests, and no abnormalities are found in the internal organs of the test animals administered pullulan. Therefore, pullulan is considered a safe food additive. Furthermore, its chemical properties are not affected by changes in pH or by heat, so that pullulan is expected to fully withstand processes such as cooking and food processing.

When only gymnemic acid is used, it must be added in relatively large amount to foodstuffs in order to achieve a sufficient inhibitory effect of glucose absorption through the intestines. This is quite uneconomical in view of the high cost of gymnemic acid.

The inventor found the fact that combined use of gymnemic acid and pullulan can exhibit a remarkable intestinal absorption inhibiting effect, in specific ratios having a low additive dose of gymnemic acid, of substantially the same level as a case of usage of a high amount of gymnemic acid. This unobvious combination serves to provide an economic advantage.

Gymnemic acid is obtained by the steps of immersing dried leaves of GS in an aqueous solution at 60° C. for about five hours adjusting the pH of the solution to 3, and collecting precipitate formed. The yield of gymnemic acid amounts to about 13 g per kg of the dried leaves.

Pullulan is manufactured by carrying out the steps of inoculating Aureobasidium pullulans in a culture medium; after sterilization, stirring and culturing in the medium under aerobic conditions; removing bacteria by filtration or the like means; decolorizing with activated carbon; concentrating in a can type vacuum concentrator; drying in a drum drier or the like means; grinding; and bolting treatment. Pullulan achieved through these steps contains 4% of salt, 10% of residual sugar and 5% of water.

BRIEF DESCRIPTION OF THE DRAWINGS

In the accompanying drawings.

EXAMPLE

Three Wistar strain male rats were peritoneally administered 30 mg/kg body weight of streptozotocin, respectively, to induce experimental diabetes in these rats, and they were subject to Oral Sucrose Tolerance Test (hereinafter referred to as "OSTT").

In the OSTT, each male rat was placed in an overnight fast condition from the day before the test day and was subject to three experiments: in the first one, it was orally administered 2 g/kg bwt of sucrose only; in the second one 2 g/kg bwt of sucrose and 0.05 g/kg bwt of gymnemic acid; and in the third one 2 g/kg bwt of sucrose, 0.05 g/kg bwt of gymnemic acid and 0.02 g/kg bwt of pullulan. In each experiment, the increment of plasma glucose (or blood glucose) was measured in the rats before administration and at the expiry of 30 minutes, 60 minutes and 120 minutes after administration.

Figure 1:
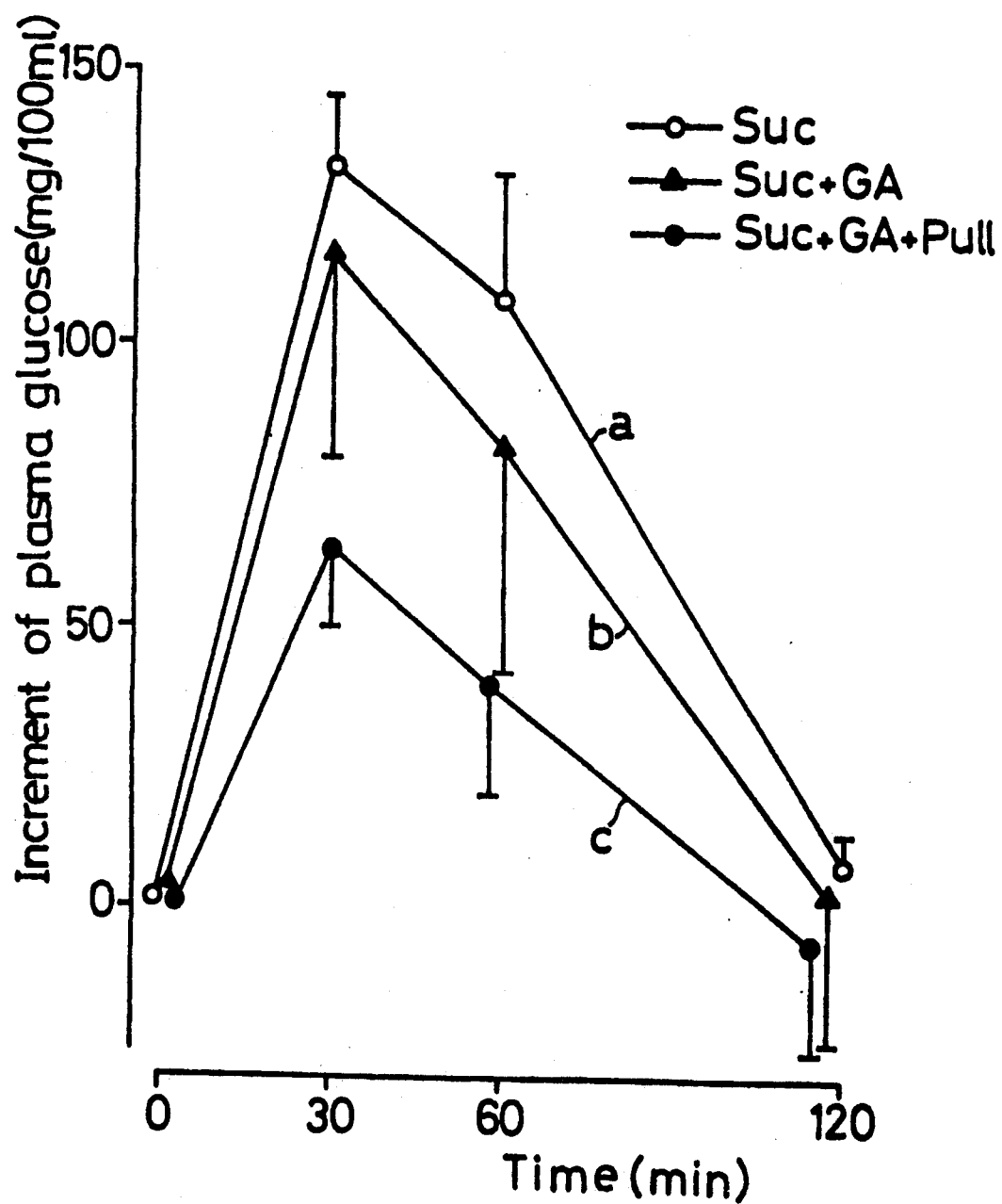
FIG. 1 is a graph showing increment of plasma glucose with passage of time.

FIG. 1 illustrates OSTT curves resulted from these measurements. Curve a is indicative of the case of administration of sucrose only, curve b shows the case of mixed administration of sucrose and gymnemic acid and curve c does of sucrose, gymnemic acid and pullulan. In this figure, vertical bars indicate standard errors.

As is evident from curve b, when a small amount of gymnemic acid has been dosed, an inhibitory effect of glucose absorption through the intestinal tract could be clearly observed as compared with curve a. However, in the case of the combination dosage of gymnemic acid and pullulan shown in curve c, the intestinal glucose absorption inhibiting effect was remarkable when compared with the case of curve a, in particular at the points of 30 and 60 minutes after administration. This inhibitory effect was far enhanced even in comparison to curve b. This results from the combined use of a small amount of gymnemic acid and a small amount of pullulan.

Next, the area under curve (hereinafter referred to as "AUC") was calculated out at the portion from 0 (fast) to 60 minutes (administered) using the OSTT curve for the case of feeding sucrose only, that is, the curve a of FIG. 1. Accordingly, this AUC represents the total amount of glucose absorbed through the intestinal tract during the period from 0 to 60 minutes after administration.

Further, AUC were calculated similarly for OSTT curves which were achieved for the cases of adding to sucrose: gymnemic acid only; gymnemic acid and 0.02 g/kg bwt of pullulan in combination; and gymnemic acid and 0.2 g/kg bwt of pullulan in combination the dose of gymnemic acid varied.

For a comparison, AUC was also calculated for the case where 0.02 g/kg bwt of pullulan was added to sucrose, similarly to the above-mentioned cases.

Figure 2:
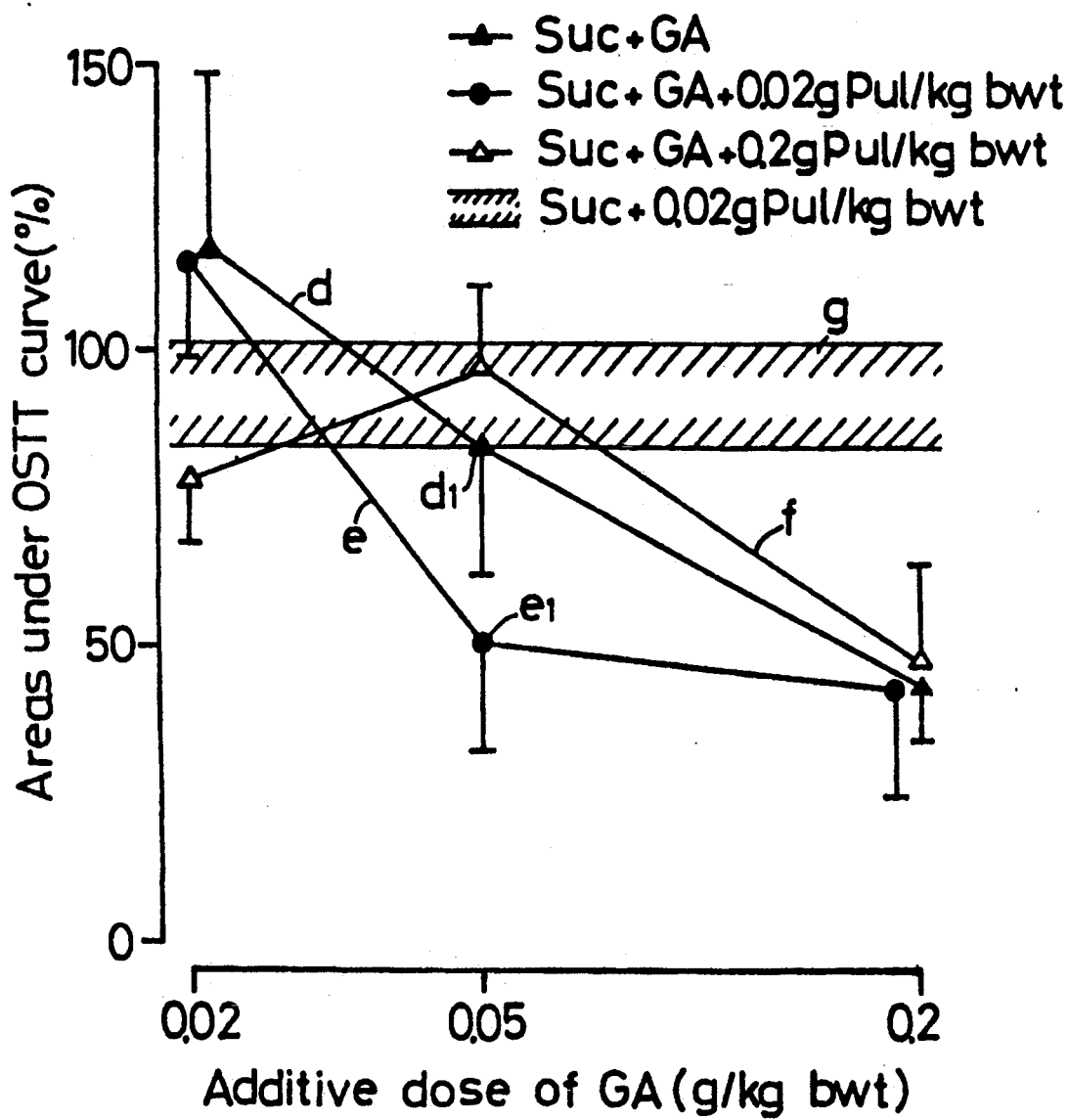
FIG. 2 is a graph showing the relationship between the additive doses of gymnemic acid and and the area under the OSTT curve.

In FIG. 2, the ordinate represents the ratio of AUC for the various cases with respect to AUC with the case of sole dosage of sucrose as a standard value of 100%, whilst the abscissa indicates the additive dose of gymnemic acid. Consequently, it can be stated that the lower the level of the calculated AUC value, the higher the intestinal absorption inhibiting effect. Incidentally, in this figure, vertical bars show standard errors.

In FIG. 2, curve d corresponds to the case of addition of gymnemic acid only, curve e shows the case of the combined addition of gymnemic acid and 0.02 g/kg bwt of pullulan and curve f shows the case of the combined addition of gymnemic acid and 0.2 g/kg bwt of pullulan. Region g shows the case in which pullulan only is added to sucrose.

In the case of the sole addition of pullulan, AUC is $92.6 \pm 18.2\%$ which indicates a mean value $\pm$ standard errors (and has the same indicates in the following description). This is almost at the same level as the standard value and provides a small effect of inhibiting glucose absorption through the intestinal tract.

As shown by curve d, AUC for the cases where male rats were administered sucrose together with additive dose of gymnemic acid in the amount of 0.02, 0.05 and 0.2 g/kg bwt, had reduced values of $117.2 \pm 54.8$, $83.9 \pm 38.1$ and $43.4 \pm 16.4\%$, respectively. Following the increase in the amount of addition of gymnemic acid, the intestinal absorption inhibiting effect against glucose is enhanced and this tendency is made remarkable when the additive dose of gymnemic acid is at a high level of 0.2 g/kg bwt.

Curve e shows that in the case of the combined use of gymnemic acid and 0.02 g/kg bwt of pullulan. There was not much of a distinctive effect when the additive dose of gymnemic acid amounts to 0.02 g/kg bwt and 0.2 g/kg bwt, as compared with the curve d for sole addition of gymnemic acid. However, a remarkable suppression of glucose absorption through intestines is observed when the additive dose of gymnemic acid is 0.05 g/kg bwt shown as at point $e_1$ at which AUC was lowered to $50.5 \pm 32.3\%$. This becomes apparent when compared with point $d_1$ of the curve d at which AUC is $83.9 \pm 38.1\%$. The inhibitory effect at point $e_1$ is substantially equivalent to the effect which would be obtained by adding 0.2 g/kg bwt of gymnemic acid only to sucrose, which is four times the amount for the case of the point $e_1$. In other words, the intestinal absorption inhibiting effect obtained in the case having 0.05 g/kg bwt of gymnemic acid and 0.02 g/kg bwt of pullulan dosed in addition to 2 g/kg bwt of sucrose substantially equals to that of the case in which four times the amount of gymnemic acid, that is, 0.2 g/kg bwt of said acid, is solely added to 2 g/kg bwt of sucrose. Accordingly, by adding relatively low cost pullulan having to a small amount of relatively low cost gymnemic acid, there can be obtained an intestinal absorption inhibitory effect against glucose that corresponds to the effect obtainable with dose of a large amount of gymnemic acid. This permits production of low-calorie foods and beverages at a low cost. Incidentally, the point $d_1$ on curve d corresponds to the curve b of FIG. 1 and the point $e_1$ on curve e corresponds to the curve c of FIG. 1, respectively.

If the amount of pullulan added was increased to 0.2 g/kg bwt, as shown by curve f, AUC was $78.1 \pm 18.4\%$ when the additive dose of gymnemic acid was 0.02 g/kg bwt, providing a slight degree of intestinal absorption inhibiting effect. When gymnemic acid was added in the amount of 0.05 g/kg bwt, the effect was almost of the same level as the case of sole addition of pullulan shown by region g. With a 0.2 g/kg bwt of additive dose of gymnemic acid, no particular effect could be seen which would be caused by addition of pullulan.

When the amount of gymnemic acid added was 0.2 g/kg bwt, AUC was substantially the same in curves d, e and f. Therefore, at this level of addition of gymnemic acid, AUC was not affected by addition or absence of pullulan or by variation in amount of pullulan. Combined use of gymnemic acid and pullulan according to the invention can bring about a remarkable intestinal absorption inhibitory effect but only when added in a specific range ratio.

From the above, it should be apparent that when a small amount of gymnemic acid and a small amount of pullulan are mixed with sucrose and the mixture is orally administered to human beings, there is attained a largely enhanced inhibitory effect against glucose absorption through their intestinal tracts.

In order to achieve this effect reliably, it is required to use 0.05–0.1 g/kg bwt of gymnemic acid and 0.002–0.05 g/kg bwt of pullulan in combination. As a preferred example, 0.05 g/kg bwt of gymnemic acid and 0.02 g/kg bwt of pullulan can be simultaneously added per 2 g/kg bwt of sucrose, as mentioned above.

From the foregoing description, it is apparent that additive dose of pullulan together with gymnemic acid can greatly enhance the effect of suppressing digestion and absorption of starch, sucrose and like substances. As low-caloric foods and beverages including these components there can be listed up, for example, tea mainly consisting of GS leaves with pullulan added thereto, liquors produced by extracting gymnemic acid using alcohol and adding thereto pullulan, cakes and candies added with gymnemic acid and pullulan and the like.

Thus, low-calorie foods and beverages obtainable according to the invention contain therein gymnemic acid and pullulan as synergistically functioning agents for inhibiting intestinal glucose absorption so that the build up of frustration for sweetness can be avoided and obesity can be prevented. Said low-calorie foods and beverages are quite effective to be fed by diabetic persons. The disclosed combination of gymnemic acid and pullulan suggests use of a small amount of the gymnemic acid and such combined use of these components can achieve a favourable intestinal absorption inhibitory effect against glucose as equivalent to the effect resulting from addition of a large amount of gymnemic acid only, thereby providing an economically advantageous situation.

What is claimed is:

1. A composition which inhibits the absorption of glucose through the intestinal tract of an animal comprising 0.05–0.1 parts by weight of gymnemic acid and 0.002–0.05 parts by weight of pullulan.

2. A carbohydrate containing foodstuff having admixed therewith 0.05–0.1 parts by weight of gymnemic acid and 0.002–0.05 parts by weight of pullulan per 2 parts by weight of carbohydrate.

3. A method of inhibiting the absorption of glucose through the intestinal tract of an animal which comprises feeding the animal 0.05–0.1 g/kg bwt gymnemic acid and 0.002–0.05 g/kg bwt pullulan together with a foodstuff containing 2 g/kg bwt of a carbohydrate which forms glucose on digestion.

* * * * *